United States Patent [19]

Schwartzman et al.

[11] 4,141,913
[45] Feb. 27, 1979

[54] METHOD OF GENERATING LOWER ALKYL AND CYCLOALKYL ISOCYANATES

[75] Inventors: Sanford Schwartzman, Tenafly; Daniel A. Lima, Bloomsbury, both of N.J.

[73] Assignee: American Carbonyl, Inc., Englewood, N.J.

[21] Appl. No.: 871,491

[22] Filed: Jan. 23, 1978

[51] Int. Cl.² ............................................. C07C 118/00
[52] U.S. Cl. ................................................. 260/453 P
[58] Field of Search ..................................... 260/453 P

[56] References Cited

U.S. PATENT DOCUMENTS

| 3,898,259 | 8/1975 | Hearsey | 260/453 P |
| 3,936,484 | 2/1976 | Rosenthal et al. | 260/453 P |

*Primary Examiner*—Dolph H. Torrence
*Attorney, Agent, or Firm*—Henry R. Lerner

[57] ABSTRACT

A method of generating lower alkyl and cycloalkyl isocyanates in situ by pyrolysis of an appropriately selected alkyl aryl urea of the formula

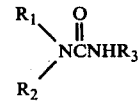

where $R_1$ aryl, $R_2$ may be either alkyl, cycloalkyl or aryl, and in which $R_3$ is the specific lower ($C_1$ through $C_6$) alkyl or cycloalkyl radical of the isocyanate selected to be generated.

7 Claims, No Drawings

METHOD OF GENERATING LOWER ALKYL AND CYCLOALKYL ISOCYANATES

This invention relates to chemical processes which generate lower alkyl and cycloalkyl isocyanates in situ.

Lower alkyl and cycloalkyl isocyanates, and especially methyl isocyanate, are well known and highly reactive organic chemicals possessing the structure $$RN=C=O$$

where R is either lower alkyl ($C_NH_{2N+1}$) or cycloalkyl ($C_NH_{2N-1}$), and N may be any whole number from one through six.

The reactivity of the —NCO grouping makes isocyanates highly desirable for use as intermediates in the manufacture of drugs, pesticides, and numerous other classes of organic chemicals. Unfortunately, the isocyanates are unusually dangerous, with the degree of hazard increasing as the alkyl grouping decreases in size. The hazards are toxicological, flammability and explosion.

In the most reactive and wisely used member of this series, methyl isocyanate, the handling precautions are so complex that they preclude use of the product except where no other synthesis route to the desired end-product is known. Because of the ease with which certain impurities can catalyze the formation of dimers and trimers, tank cars of methyl isocyanate can liberate enough heat of reaction to blow up. The isocyanates, in addition to their general toxicity, are powerful lachrymators. Thus, the material handling costs associated with the safe unloading, storage and handling of these isocyanates, while varying in degree, are so onerous as to make their use an unreasonably costly hazard at best, and commercially unfeasible at worst.

According to the present invention, essentially all of these hazards may be eliminated. The teachings may be practiced by providing, rather than the lower alkyl isocyanates in their essentially commercially pure, but highly dangerous form, a urea derivative which may be easily and safely handled, transported and stored, and from which, by simple pyrolysis, the appropriate isocyanate may be generated in situ, in quantities only as needed, and reacted more or less directly to produce the desired end-product, whether drug, pesticide, or other useful class of product.

A further advantage of this invention is that there is rather wide latitude in the choice of the urea used as the isocyanate generator, such that it is practicable to provide a product which may be liquid or solid, and which pyrolyzes to liberate the isocyanate at a desired temperature range.

A further advantage of this invention is that the residue remaining after pyrolysis is recyclable -- that is, it may be returned to the producer, using only ordinary handling precautions and commonly available equipment, purified if necessary by simple distillation, and used again to produce more of the isocyanate generating compound.

The process which comprises this invention uses alkyl aryl ureas of the general formula

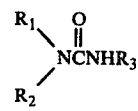

where $R_1$ is an aryl, $R_2$ may be aryl or alkyl, and $R_3$ is the specific lower alkyl or cycloalkyl radical appearing in the desired isocyanate.

Upon heating to the temperature necessary to cause pyrolysis, the urea splits

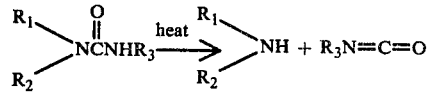

At the temperature of pyrolysis the $R_3$ isocyanate distills out as a gas, and may be easily condensed, if desired, and fed into whatever equipment is used for the subsequent reactions which convert the isocyanates to the drugs, pesticides or whatever, without exposure of the isocyanates as generated to either the production workers or the environment. The remaining $R_1$-containing aryl amine, depending on its physical properties, may be returned in solid or liquid form to the urea producer's plant, for re-use.

The ureas used in the process of this invention may be conveniently prepared by reacting the

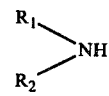

with an excess of phosgene, under conditions well known to those skilled in the art, to yield the corresponding carbamyl chloride, and then further reacting the carbamyl chloride thus produced with the desired $R_3$ primary amine, to yield directly the desired urea.

By way of illustration, one mole of diphenylamine is reacted with a 10% molar excess of phosgene in a suitable solvent such as monochlorobenzene, to yield diphenylcarbamyl chloride. The carbamyl chloride thus produced is reacted further with n-propyl amine in stoichiometric amounts, in the presence of a mole of caustic soda. Diphenyl propyl urea (DPPU) is formed in essentially stoichiometric amounts. The DPPU formed may be either separated from the solvent or, if desired, supplied as a solution in its reaction solvent. DPPU pyrolyzes at 210°–220° C. to yield n-propyl isocyanate of 99% purity and greater than 90% yield. The diphenylamine remaining may be returned easily in tankcars or tankwagons for reprocessing.

While there is herein shown and described the preferred embodiment of the invention, it will be understood that the invention may be embodied otherwise than as herein specifically illustrated or described, and that in illustrated embodiment certain changes in the details of construction and in the form and arrangement of parts may be made without departing from the underlying idea or principles of this invention within the scope of the appended claims.

Having thus described our invention, what we claim and desire to secure by Letters Patent is:

1. A method of generating lower alkyl and cycloalkyl isocyanates in situ consisting essentially of pyrolyzing, in the absence of solvent an appropriately selected aryl urea of the formula

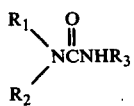

wherein $R_1$ is aryl, $R_2$ may be either alkyl, cycloalkyl or aryl, and in which $R_3$ is the specific lower ($C_1$ through $C_6$) alkyl or cycloalkyl radical of the isocyanate selected to be generated, said urea being characterized by selection of the

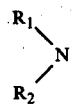

moiety so that only the $R_3NCO$ moiety of said urea is vaporized at the pyrolysis temperature.

2. The method of claim 1 above, in which $R_1$ and $R_2$ are phenyl groups, and $R_3$ is methyl.

3. The method of claim 1 above, in which $R_1$ and $R_2$ are phenyl groups, and $R_3$ is n-propyl.

4. The method of claim 1 above, in which $R_1$ is phenyl, $R_2$ is methyl, and $R_3$ is methyl.

5. The method of claim 1 above, in which $R_1$ is phenyl, $R_2$ is methyl, and $R_3$ is n-propyl.

6. The method of claim 1 above, in which $R_1$ is phenyl, $R_2$ is ethyl, and $R_3$ is methyl.

7. The method of claim 1 above, in which $R_1$ is phenyl, $R_2$ is ethyl, and $R_3$ is n-propyl.

* * * * *